(12) United States Patent
Kolb

(10) Patent No.: US 9,936,797 B2
(45) Date of Patent: Apr. 10, 2018

(54) ORAL CARE DISPENSER AND ORAL CARE SYSTEM

(71) Applicant: Colgate-Palmolive Company, New York, NY (US)

(72) Inventor: Matthew Lee Kolb, Upper Black Eddy, PA (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/106,501

(22) PCT Filed: Dec. 19, 2013

(86) PCT No.: PCT/US2013/076586
§ 371 (c)(1),
(2) Date: Jun. 20, 2016

(87) PCT Pub. No.: WO2015/094291
PCT Pub. Date: Jun. 25, 2015

(65) Prior Publication Data
US 2016/0331110 A1    Nov. 17, 2016

(51) Int. Cl.
*A46B 11/02*    (2006.01)
*A46B 11/00*    (2006.01)
(Continued)

(52) U.S. Cl.
CPC ............ *A46B 11/001* (2013.01); *A46B 9/04* (2013.01); *A46B 11/002* (2013.01); *A46B 11/0024* (2013.01); *A46B 11/0041* (2013.01); *A46B 11/0055* (2013.01); *A61C 17/227* (2013.01); *A61C 19/063* (2013.01); *A61C 19/066* (2013.01); *A46B 2200/1066* (2013.01)

(58) Field of Classification Search
CPC ..................... A46B 11/002; A46B 11/0065
USPC ..................................... 401/188 R
See application file for complete search history.

(56) References Cited

U.S. PATENT DOCUMENTS

| 4,733,983 A | 3/1988 | Hertrampf |
| 6,241,412 B1 * | 6/2001 | Spies ................. A46B 11/002 206/532 |

(Continued)

FOREIGN PATENT DOCUMENTS

| FR | 2600513 | 12/1987 |
| KR | 101310337 | 9/2013 |
| WO | WO2012082183 | 6/2012 |

OTHER PUBLICATIONS

Corresponding Search Report for PCT/US2013/076586 dated Oct. 20 2014.

*Primary Examiner* — Jennifer C Chiang

(57) ABSTRACT

An oral care dispenser for dispensing an oral care fluid. The dispenser may include: a housing defining a cavity; a wall in the cavity, the wall dividing the cavity into first and second reservoirs of variable volume, the first reservoir containing an oral care fluid; a first opening in fluid communication with the first reservoir, wherein the oral care fluid is dispensable from the dispenser through the first opening; a second opening in fluid communication with the second reservoir; and an actuator operable to dispense the oral care fluid through the first opening. In an embodiment, the oral care dispenser may form a part of a system that includes an oral care implement, such as a toothbrush.

20 Claims, 5 Drawing Sheets

(51) Int. Cl.
*A46B 9/04* (2006.01)
*A61C 17/22* (2006.01)
*A61C 19/06* (2006.01)

(56) References Cited

U.S. PATENT DOCUMENTS

| | | |
|---|---|---|
| 6,257,791 B1 | 7/2001 | Scamard |
| 8,087,843 B2 * | 1/2012 | Ottaviani ........... A46B 11/0041 15/22.1 |
| 9,022,680 B1 * | 5/2015 | Lubyanitskiy ..... A46B 11/0086 401/142 |
| 9,173,477 B2 | 11/2015 | Jimenez et al. |
| 2005/0036821 A1 | 2/2005 | Pfenniger et al. |
| 2005/0220530 A1 | 10/2005 | Carmona |
| 2012/0114410 A1 | 5/2012 | Jimenez et al. |
| 2012/0301209 A1 | 11/2012 | Fattori |
| 2013/0130196 A1 | 5/2013 | Joyashiki et al. |

* cited by examiner

ORAL CARE DISPENSER AND ORAL CARE SYSTEM

CROSS-REFERENCE TO RELATED PATENT APPLICATIONS

The present application is a U.S. national stage application under 35 U.S.C. § 371 of PCT Application No. PCT/US2013/076586, filed Dec. 19, 2013, the entirety of which is incorporated herein by reference.

BACKGROUND

The present invention relates to an oral care dispenser for dispensing an oral care fluid, such as an oral care fluid comprising a whitening agent, and to an oral care system comprising such an oral care dispenser and an oral care implement.

It is known to provide an oral care dispenser that is operable to dispense an oral care fluid, such as an oral care fluid comprising a whitening agent, to a user's teeth. Some known such oral care dispensers are difficult to operate to dispense a suitable, small volume of the oral care fluid. This can result in application of a volume of the oral care fluid to a user's teeth greater than a volume actually required for the oral care fluid to have the desired effect, such as teeth whitening. Accordingly, some of the oral care fluid is wasted. Oral care systems comprising an oral care implement, such as a toothbrush, and an oral care dispenser operable to dispense an oral care fluid, and connectable to the oral care implement, are known. Some known such oral care systems suffer from the problem that the dispenser accidentally may be actuated to dispense some of the oral care fluid when it is not desired to do so, such as when the oral care dispenser is connected to the oral care implement.

There is a need for an oral care dispenser that is more easily operable to dispense a suitable volume of an oral care fluid. There also is a need for an oral care system comprising an oral care implement and an oral care dispenser connectable to the oral care implement, which oral care system helps prevent accidental actuation of the dispenser.

BRIEF SUMMARY

An embodiment of the present invention provides a first oral care dispenser, comprising: a housing defining a cavity; a wall of flexible material in the cavity, the wall dividing the cavity into first and second reservoirs of variable volume, the first reservoir containing an oral care fluid; a first opening in fluid communication with the first reservoir, wherein the oral care fluid is dispensable from the dispenser through the first opening; a second opening in fluid communication with the second reservoir via a check valve that permits flow into the second reservoir from an exterior of the dispenser and restricts flow from the second reservoir to the exterior of the dispenser; and an actuator operable to dispense the oral care fluid through the first opening.

Optionally, the actuator is operable to push air into the second reservoir through the check valve.

Optionally, the actuator comprises a wall defining the second opening and a chamber fluidly connecting the second opening with the check valve.

Optionally, the chamber is of variable volume. Further optionally, the actuator is operable to reduce the volume of the chamber when the second opening is blocked, thereby to push air from the chamber into the second reservoir through the check valve.

Optionally, the actuator comprises flexible material defining the chamber of variable volume.

Optionally, the actuator defines the first opening and is movable relative to the housing to reduce the volume of the first reservoir, thereby to dispense the oral care fluid through the first opening.

Another embodiment of the present invention provides a second oral care dispenser, comprising: a housing defining a cavity; a wall in the cavity, the wall dividing the cavity into first and second reservoirs of variable volume, the first reservoir containing an oral care fluid; a first opening in fluid communication with the first reservoir, wherein the oral care fluid is dispensable from the dispenser through the first opening; a second opening in fluid communication with the second reservoir via a check valve that permits flow into the second reservoir from an exterior of the dispenser and restricts flow from the second reservoir to the exterior of the dispenser; and an actuator operable to dispense the oral care fluid through the first opening; wherein the actuator defines the first opening and is movable relative to the housing to reduce the volume of the first reservoir, thereby to dispense the oral care fluid through the first opening.

Optionally, the wall comprises a wall of flexible material.

Optionally, in either of the first and second oral care dispensers, the actuator is operable to pull air into the second reservoir through the check valve.

Optionally, in either of the first and second oral care dispensers, the housing defines the second opening and a chamber of fixed volume fluidly connecting the second opening with the check valve.

Optionally, in either of the first and second oral care dispensers, the wall of flexible material comprises a deformable vessel with an orifice in fluid communication with the first opening. Further optionally, the vessel is deformable according to a predetermined pattern of collapse, and/or the vessel comprises a bellows.

Optionally, in either of the first and second oral care dispensers, the check valve comprises one of: a diaphragm check valve, a ball check valve, a swing check valve, and a duckbill check valve.

Optionally, in either of the first and second oral care dispensers, the first opening is in fluid communication with the first reservoir via a second check valve that restricts flow into the first reservoir from an exterior of the dispenser and permits flow from the first reservoir to the exterior of the dispenser.

Optionally, either of the first and second oral care dispensers comprises a flexible or resilient applicator, wherein the first opening is formed in the applicator.

Optionally, in either of the first and second oral care dispensers, the first opening is at a distal end portion of the dispenser and the second opening is at a proximal end portion of the dispenser.

Optionally, in either of the first and second oral care dispensers, the oral care fluid comprises one or more oral care agents selected from the group consisting of: antibacterial agents; oxidative or whitening agents; enamel strengthening or repair agents; tooth erosion preventing agents; tooth anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof.

Another embodiment of the present invention provides a first oral care system, comprising: either one of the first and second oral care dispensers; and an oral care implement; wherein the oral care dispenser is movable relative to the oral care implement between a storage state, at which a portion of the oral care implement blocks the first opening of the oral care dispenser from an exterior of the oral care system, and an application state, at which the first opening of the oral care dispenser is not blocked by the oral care implement.

A further embodiment of the present invention provides a second oral care system, comprising: an oral care dispenser comprising: a housing defining a cavity; a wall in the cavity, the wall dividing the cavity into first and second reservoirs of variable volume, the first reservoir containing an oral care fluid; a first opening in fluid communication with the first reservoir, wherein the oral care fluid is dispensable from the dispenser through the first opening; a second opening in fluid communication with the second reservoir; and an actuator operable to dispense the oral care fluid through the first opening; and an oral care implement; wherein the oral care dispenser is movable relative to the oral care implement between a storage state, at which a portion of the oral care implement blocks the second opening of the oral care dispenser from an exterior of the oral care system, and an application state, at which the second opening of the oral care dispenser is not blocked by the oral care implement.

Optionally, the wall comprises a wall of flexible material.

Optionally, the second opening is in fluid communication with the second reservoir via a check valve that permits flow into the second reservoir from an exterior of the dispenser and restricts flow from the second reservoir to the exterior of the dispenser.

Optionally, when the oral care dispenser is in the storage state, a portion of the oral care implement blocks the first opening of the oral care dispenser from the exterior of the oral care system. Further optionally, when the oral care dispenser is in the application state, the first opening of the oral care dispenser is not blocked by the oral care implement.

Optionally, the oral care dispenser of the second oral care system is either one of the first and second oral care dispensers.

Optionally, in either of the first and second oral care systems, when the oral care dispenser is in the application state, the oral care dispenser is detached from the oral care implement.

Optionally, in either of the first and second oral care systems, the oral care implement comprises a toothbrush.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

In the following description, each of the exemplary embodiments of the oral care system of the invention comprises a manually-operated oral care implement, more specifically a manually-operated toothbrush. However, in variations to these embodiments, the oral care system could instead comprise a powered implement, such as a powered toothbrush, wherein one or more oral care elements provided to a head of the implement are drivable so as to be moved relative to a handle of the implement. In still further embodiments, the oral care system could instead comprise other forms of oral care implement, such as a soft-tissue cleaner, a tooth polisher, an interdental brush, a tongue scraper, or another implement designed for oral care. It is to be understood that other embodiments may be utilised, and that structural and functional modifications may be made without departing from the scope of the present invention.

Figure 1:
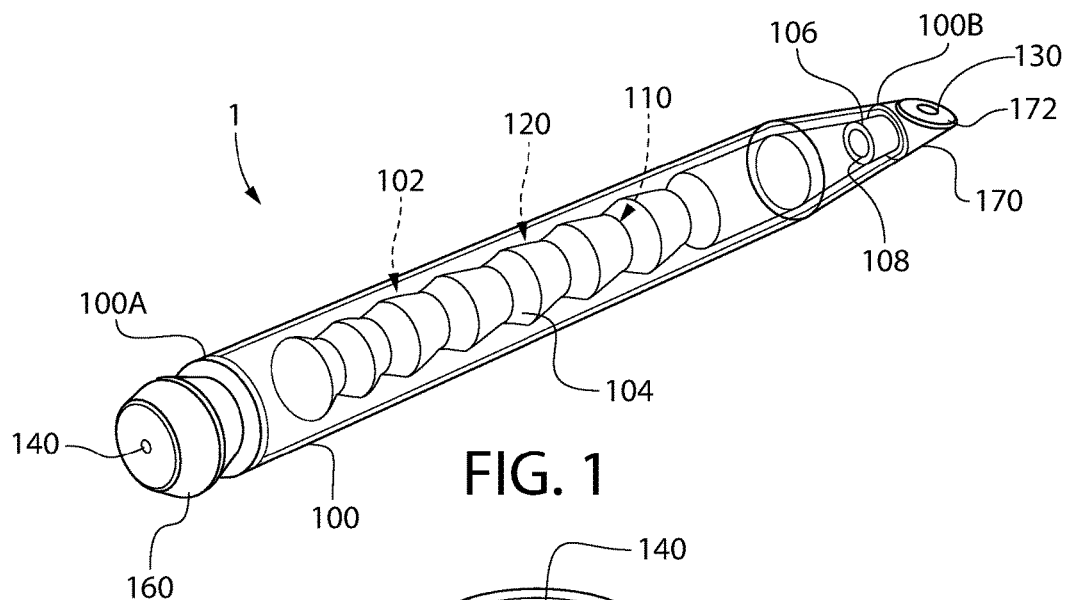
FIG. 1 shows a perspective view of an oral care dispenser according to an exemplary embodiment of the present invention, with an actuator of the dispenser in a first state.
Figure 2:
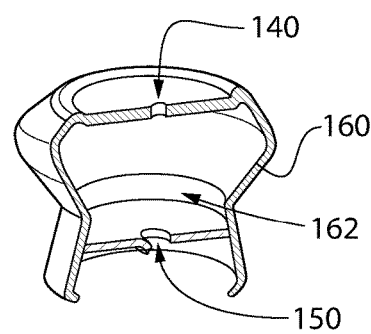
FIG. 2 shows a close-up cross-sectional perspective view of a body of the oral care dispenser of FIG. 1.
Figure 3:
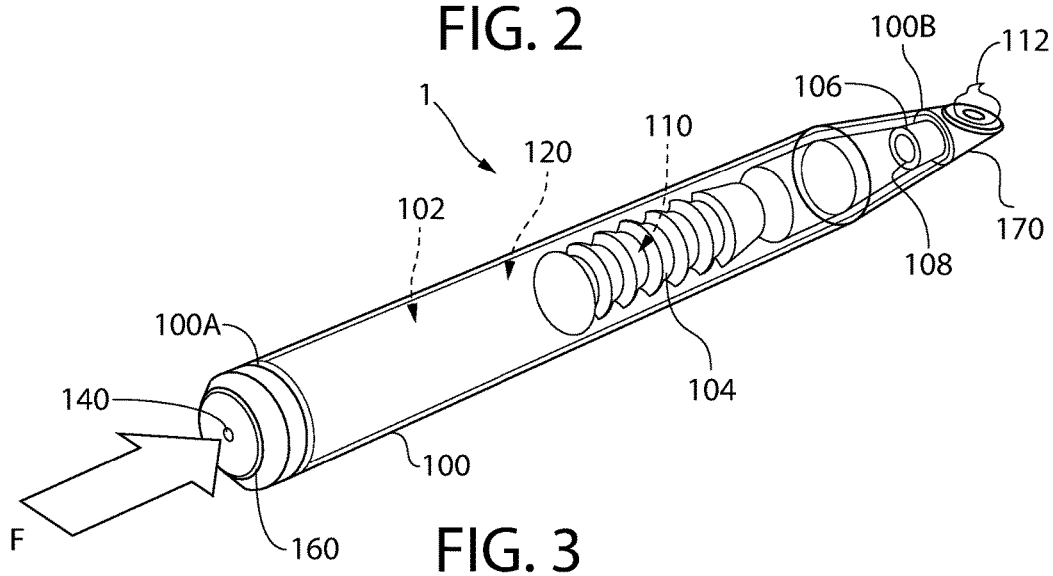
FIG. 3 shows a perspective view of the oral care dispenser of FIG. 1, with the actuator of the dispenser in a second state.

FIGS. 1 to 3 illustrate an oral care dispenser according to an exemplary embodiment of the present invention, generally designated with the reference numeral 1. The oral care dispenser 1 comprises a substantially rigid tube, or housing, 100 formed of a plastic, specifically a thermoplastic polymer, more specifically polypropylene (PP). In some variations to the illustrated embodiment, the housing 100 may instead or additionally be formed of a different material, such as a different plastic or thermoplastic polymer. For example, the housing 100 may instead or additionally be formed of any one or more of the following materials: polypropylene (PP), polyethylene, polyamide, polyester, cellulosics, styrene-acrylonitrile (SAN), acrylic, and acrylonitrile butadiene styrene (ABS). While in the illustrated embodiment the housing 100 is transparent, in variations to the illustrated embodiment the housing 100 may be translucent or opaque. Nevertheless, it is preferable that the housing 100 be substantially rigid.

In the illustrated embodiment, a majority of the housing 100 extending from a proximal end 100a of the housing 100 is defined by circular inner and outer surfaces. The housing 100 tapers towards a distal end 100b of the housing 100, so that a cross-sectional area of the housing 100 reduces with increased proximity to the distal end 100b. In other embodiments, all or a majority of the housing 100 may instead be defined by elliptical inner and outer surfaces, polygonal inner and outer surfaces, or irregular inner and outer surfaces.

The housing 100, and more specifically the inner surface of the housing 100, defines a cavity 102. In the illustrated embodiment, the cavity 102 has a circular cross-sectional shape. In other embodiments, the cross-sectional shape of the cavity 102 may instead be a different shape, such as elliptical, polygonal, or irregular. The cavity 102 is visible through the transparent material of the housing 100. Within the cavity 102 is a wall 104 of flexible material dividing the cavity 102 into first and second reservoirs 110, 120. The wall 104 comprises a vessel 104 that is deformable according to a predetermined pattern of collapse, and in the illustrated embodiment comprises a bellows 104. In the illustrated embodiment the wall 104 is opaque, but in variations to the illustrated embodiment the wall 104 may be transparent or translucent. Each of the first and second reservoirs 110, 120 is of variable volume, as will be better understood on consideration of the further description below. The wall 104 surrounds the first reservoir 110. A portion of the second reservoir 120 is closer to the proximal end 100a of the housing 100 than the first reservoir 110, and another portion of the second reservoir 120 surrounds the wall 104 and the first reservoir 110.

The first reservoir 110 contains, indeed is full of, an oral care fluid 112 comprising one or more oral care agents. The oral care fluid 112 may be in any fluid form, such as a paste, a gel, or a liquid. In the illustrated embodiment, the oral care agent comprised in the oral care fluid is a whitening agent, such as peroxide containing tooth whitening compositions. However, any suitable oral care agent can be used in embodiments of the present invention. In variations to the illustrated embodiment, the oral care fluid may comprise one or more oral care agents selected from the group consisting of: antibacterial agents; oxidative or whitening agents; enamel strengthening or repair agents; tooth erosion preventing agents; tooth anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof. The oral care fluid preferably is free of (i.e., is not) toothpaste. Preferably, the oral care fluid is intended to provide supplemental oral care benefits in addition to merely brushing one's teeth.

At a distal end portion of the dispenser 1, and more specifically attached to the distal end 100b of the housing 100, the dispenser 1 comprises a flexible and resilient applicator 170 formed of an elastomeric material, such as an elastomer, a thermoplastic elastomer (TPE), or styrene-ethylene/butylene-styrene (SEBS). A first opening 130 of the dispenser 1 is formed in, indeed through, a surface 172 of the applicator 170, and the first opening 130 is at the distal end portion of the dispenser 1. In the illustrated embodiment, the surface 172 of the applicator 170 is planar, but in other embodiments the surface 172 could be undulating or comprise one or more projections, fingers or nubs extending therefrom and surrounding the first opening 130. The first opening 130 is in fluid communication with the first reservoir 110 and with an exterior of the dispenser 1, and the oral care fluid 112 is dispensable from the dispenser 1 through the first opening 130. More specifically, a rim 106 of the bellows 104 defines an orifice 108 of the bellows 104 in fluid communication with the first opening 130, and a full circumference or perimeter of the rim 106 is fixed to the applicator 170 to isolate the first opening 130 and the first reservoir 110 from the second reservoir 120. The first reservoir 110 is in fluid communication with the exterior of the dispenser 1 only via the orifice 108 and the first opening 130, in that order. In variations to the illustrated embodiment, the full circumference or perimeter of the rim 106 is fixed to the inner surface of the housing 100 to isolate the first opening 130 and the first reservoir 110 from the second reservoir 120.

At a proximal end portion of the dispenser 1, and more specifically attached to the proximal end 100a of the housing 100, the dispenser 1 comprises a flexible and resilient body formed of an elastomeric material, such as an elastomer, a thermoplastic elastomer (TPE), or styrene-ethylene/butylene-styrene (SEBS). The body comprises an actuator 160 that is operable to dispense the oral care fluid 112 through the first opening 130, as will be described below. A second opening 140 of the dispenser 1 is defined by a wall of the actuator 160, is in fluid communication with the exterior of the dispenser 1, and is at the proximal end portion of the dispenser 1. The second opening 140 also is in fluid communication with the second reservoir 120 via a check valve, or one-way valve, 150 that permits flow into the second reservoir 120 from the exterior of the dispenser 1 and restricts, preferably prevents, flow from the second reservoir 120 to the exterior of the dispenser 1. The check valve 150 is formed integrally with the actuator 160 as part of the body, and is at a fixed location relative to the housing 100. In the illustrated embodiment, the check valve 150 comprises a diaphragm check valve 150. In other embodiments, the check valve 150 may comprise any one of a ball check valve, a swing check valve, and a duckbill check valve.

Although not present in the illustrated embodiment, in variations to the illustrated embodiment, the first opening 130 may be in fluid communication with the first reservoir 110 via a second check valve that restricts, preferably prevents, flow into the first reservoir 110 from the exterior of the dispenser 1 and permits flow from the first reservoir 110 to the exterior of the dispenser 1. Such a second check valve may comprise any one of diaphragm check valve, a ball check valve, a swing check valve, and a duckbill check valve.

The actuator 160 comprises flexible and resilient material defining a chamber 162 of variable volume that fluidly connects the second opening 140 with the check valve 150. A full circumference or perimeter of the body is fixed to the proximal end 100a of the housing 100 to isolate the second reservoir 120 from the exterior of the dispenser 1, other than via the check valve 150, the chamber 162 and the second opening 140. The second reservoir 120 is in fluid communication with the exterior of the dispenser 1 only via the check valve 150, the chamber 162 and the second opening 140, in that order.

In FIGS. 1 and 2, the oral care dispenser 1 is shown with the actuator 160 in a first, relaxed state. As mentioned above, the actuator 160 is operable to dispense the oral care fluid 112 through the first opening 130. More specifically, when the second opening 140 is blocked e.g. by a user's thumb or finger, the user can apply a force F, sufficient to overcome the resiliency of the material defining the chamber 162, to the wall of the actuator 160 defining the second opening 140 to reduce the volume of the chamber 162. This increases the pressure of air present in the chamber 162 and causes the actuator 160 to enter the second state shown in FIG. 3. As will be apparent to the skilled person on consideration of the full present disclosure, the increased pressure of the air in the chamber 162 causes the air in the chamber 162 to apply a force to the check valve 150 to overcome the resilience of the check valve 150. The air in the chamber 162 thus then passes through the check valve 150 into the second reservoir 120, which, in turn, increases the pressure of air present in the second reservoir 120. The increased pressure of the air in the second reservoir 120 causes the air in the second reservoir 120 to apply a force to the bellows 104 to cause the volume of the first reservoir 110 within the bellows 104 to be reduced until the pressures in the first and second reservoirs 110, 120 are substantially equal. The reduction of the volume of the first reservoir 110 causes some of the oral care fluid 112 within the first reservoir 110 to be pushed through the first opening 130, and thus dispensed from the dispenser 1 to the exterior of the dispenser 1, such as onto a user's teeth or other surface in the oral cavity, as shown in FIG. 3.

It will be understood that the actuator 160 thus is operable to dispense a predetermined metered volume or dose of the oral care fluid 112 through the first opening 130, so that the dispenser 1 is more easily operable to dispense a suitable volume of the oral care fluid 112. The predetermined metered volume is that volume of the oral care fluid 112 displaced from the first reservoir 110 by the increased volume of air introduced to the second reservoir 120, which in turn substantially equals the volume of air pushed from the chamber 162 of the actuator 160 into the second reservoir 120.

When the user subsequently unblocks the second opening 140 and reduces or removes the force F applied to the wall of the actuator 160 defining the second opening 140, air is permitted to enter the chamber 162 via the second opening 140 and the resilience of the material defining the chamber 162 causes the chamber 162 to expand, yet the check valve 150 prevents air returning from the second reservoir 120 into the chamber 162. The actuator 160 thus returns to the first, relaxed state shown in FIGS. 1 and 2.

Figure 4A:
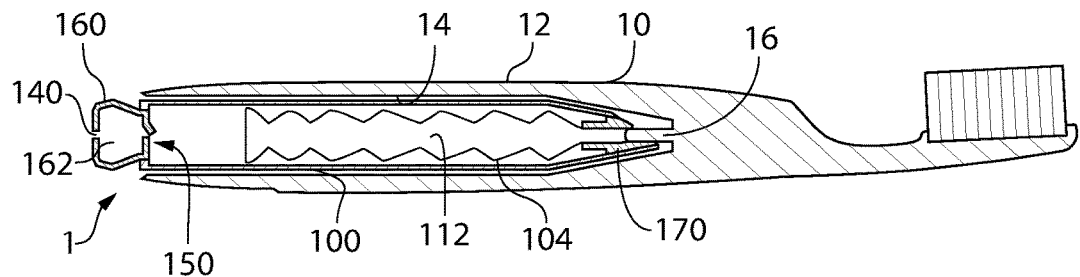
FIG. 4A shows a cross-sectional view of an oral care system according to an exemplary embodiment of the present invention, with the oral care dispenser of the system in a storage state relative to a toothbrush of the system.
Figure 4B:
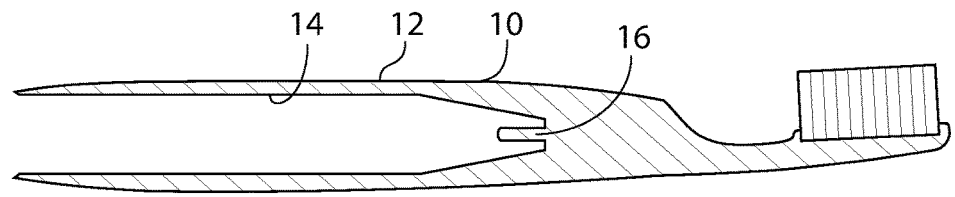
FIG. 4B shows a cross-sectional view of the oral care system of FIG. 4A, with the oral care dispenser in an application state relative to the toothbrush.
Figure 4B:
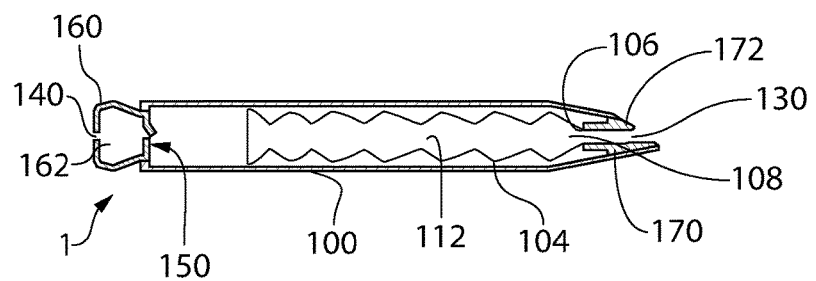

Cross sections of an oral care system according to an exemplary embodiment of the present invention are shown in FIGS. 4A and 4B. The oral care system comprises the oral care dispenser 1 shown in FIGS. 1 to 3 and an oral care implement 10 comprising a toothbrush. The toothbrush 10 comprises a handle 12, a cavity 14 in the handle 12 with an opening to an exterior of the toothbrush 10 at a first longitudinal end of the handle 12, and a head 18 comprising oral care elements, such as bristles, at a second longitudinal end of the handle 12. The oral care dispenser 1 is movable relative to the toothbrush 10 between a storage state, as shown in FIG. 4A, at which a portion of the toothbrush 10, namely a plug 16 within the cavity 14 in the handle 12 of the toothbrush 10, blocks the first opening 130 of the oral care dispenser 1 from an exterior of the oral care system, and an application state, as shown in FIG. 4B, at which the oral care dispenser 1 is detached from the toothbrush 10 and the first opening 130 of the oral care dispenser 1 is not blocked by the toothbrush 10. Thus, the oral care system has a mechanism that helps prevent accidental actuation of the dispenser 1 to dispense some of the oral care fluid 112.

In variations to the embodiment shown in FIGS. 4A and 4B, the plug 16 may be omitted, and the first opening 130 may be blocked from the exterior of the oral care system by a portion of the cavity 14 forming a seal around the full perimeter or circumference of the applicator 170 or housing 100 of the dispenser 1. The toothbrush 10 and the dispenser 1 may comprise respective cooperating retaining members, for detachably locking or retaining the dispenser 1 in the storage state relative to the toothbrush 10. In further variations to the illustrated embodiment, when the oral care dispenser 1 is in the storage state, a portion of the toothbrush 10, such as a cap that is movable relative to, detachable from, the handle, blocks the second opening 140 of the oral care dispenser 1 from the exterior of the oral care system, and when the oral care dispenser 1 is in the application state, the second opening 140 of the oral care dispenser 1 is not blocked by the toothbrush 10. Thus, the oral care system may have a still further mechanism to help prevent accidental actuation of the dispenser 1 to dispense some of the oral care fluid 112.

Figure 5:
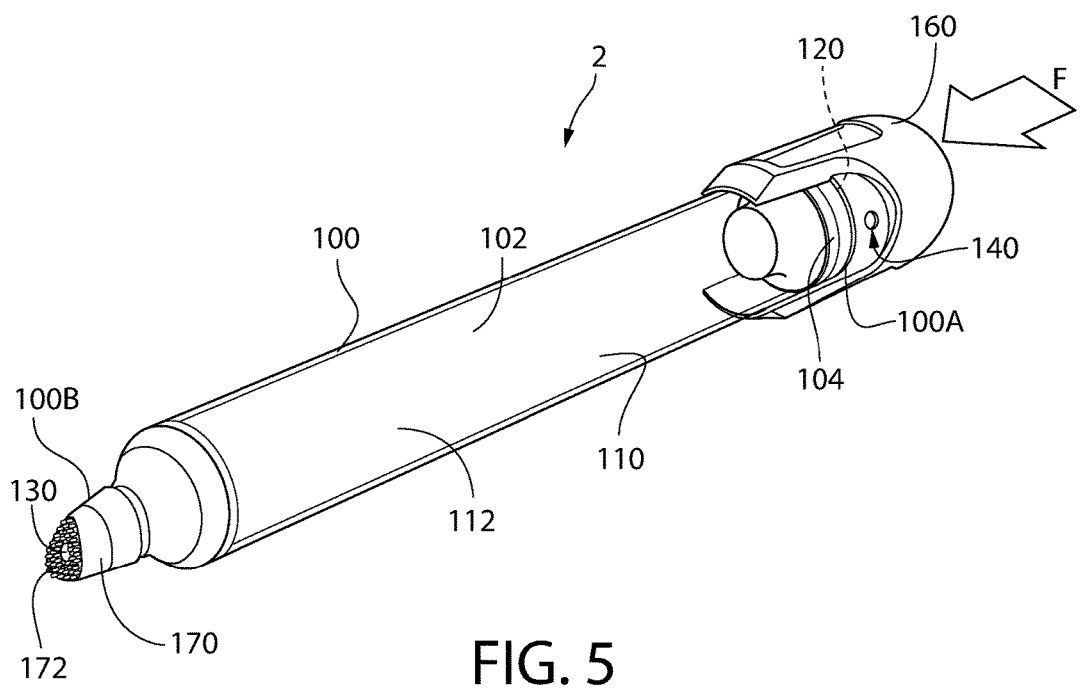
FIG. 5 shows a perspective view of an oral care dispenser of an oral care system according to another exemplary embodiment of the present invention.
Figure 6:
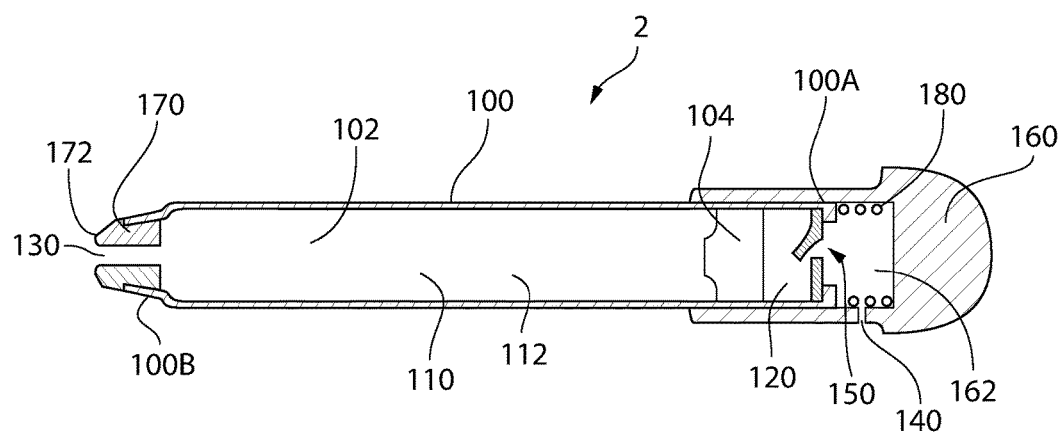
FIG. 6 shows a cross-sectional view of the oral care dispenser of FIG. 5.

FIGS. 5 and 6 illustrate an oral care dispenser 2 of an oral care system according to another exemplary embodiment of the present invention. Like reference numerals used in FIGS. 5 and 6 and FIGS. 1 to 3 indicate like components. The oral care dispenser 2 shares many features with the oral care dispenser 1.

The oral care dispenser 2 comprises a substantially rigid tube, or housing, 100 formed of a plastic, specifically a thermoplastic polymer, more specifically polypropylene (PP). In some variations to the illustrated embodiment, the housing 100 may instead or additionally be formed of a different material, such as a different plastic or thermoplastic polymer. For example, the housing 100 may instead or additionally be formed of any one or more of the following materials: polypropylene (PP), polyethylene, polyamide, polyester, cellulosics, styrene-acrylonitrile (SAN), acrylic, and acrylonitrile butadiene styrene (ABS). While in the illustrated embodiment the housing 100 is transparent, in variations to the illustrated embodiment the housing 100 may be translucent or opaque. Nevertheless, it is preferable that the housing 100 be substantially rigid.

In the illustrated embodiment, a majority of the housing 100 extending from a proximal end 100a of the housing 100 is defined by circular inner and outer surfaces. The housing 100 tapers towards a distal end 100b of the housing 100, so that a cross-sectional area of the housing 100 reduces with increased proximity to the distal end 100b. In other embodiments, all or a majority of the housing 100 may instead be defined by elliptical inner and outer surfaces, polygonal inner and outer surfaces, or irregular inner and outer surfaces.

The housing 100, and more specifically the inner surface of the housing 100, defines a cavity 102. In the illustrated embodiment, the cavity 102 has a circular cross-sectional shape. In other embodiments, the cross-sectional shape of the cavity 102 may instead be a different shape, such as elliptical, polygonal, or irregular. The cavity 102 is visible through the transparent material of the housing 100. Within the cavity 102 is a piston comprising a substantially rigid wall 104, which wall 104 divides the cavity 102 into first and second reservoirs 110, 120. Each of the first and second reservoirs 110, 120 is of variable volume, as will be better understood on consideration of the further description below.

The first reservoir 110 contains, indeed is full of, an oral care fluid 112 comprising one or more oral care agents. The oral care fluid 112 may be in any fluid form, such as a paste, a gel, or a liquid. In the illustrated embodiment, the oral care agent comprised in the oral care fluid is a whitening agent, such as peroxide containing tooth whitening compositions. However, any suitable oral care agent can be used in embodiments of the present invention. In variations to the illustrated embodiment, the oral care fluid may comprise one or more oral care agents selected from the group consisting of: antibacterial agents; oxidative or whitening agents; enamel strengthening or repair agents; tooth erosion preventing agents; tooth anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof. The oral care fluid preferably is free of (i.e., is not) toothpaste. Preferably, the oral care fluid is intended to provide supplemental oral care benefits in addition to merely brushing one's teeth.

At a distal end portion of the dispenser 2, and more specifically attached to the distal end 100b of the housing 100, the dispenser 2 comprises a flexible and resilient applicator 170 formed of an elastomeric material, such as an elastomer, a thermoplastic elastomer (TPE), or styrene-ethylene/butylene-styrene (SEBS). A first opening 130 of the dispenser 2 is formed in, indeed through, a surface 172 of the applicator 170, and the first opening 130 is at the distal end portion of the dispenser 2. In the illustrated embodiment, the surface 172 of the applicator 170 comprises a plurality of nubs or projections surrounding the first opening 130, but in other embodiments the surface 172 could be planar. The first opening 130 is in fluid communication with the first reservoir 110 and with an exterior of the dispenser 2, and the oral care fluid 112 is dispensable from the dispenser 2 through the first opening 130. More specifically, the first reservoir 110 is in fluid communication with the exterior of the dispenser 2 only via the first opening 130.

At a proximal end portion of the dispenser 2, and more specifically movably attached to the proximal end 100a of the housing 100, the dispenser 2 comprises a rigid actuator 160 formed of a plastic, specifically a thermoplastic polymer, more specifically polypropylene (PP). In some variations to the illustrated embodiment, the actuator 160 may instead or additionally be formed of a different material, such as a different plastic or thermoplastic polymer. For example, the actuator 160 may instead or additionally be formed of any one or more of the following materials: polypropylene (PP), polyethylene, polyamide, polyester, cellulosics, styrene-acrylonitrile (SAN), acrylic, and acrylonitrile butadiene styrene (ABS). While in the illustrated embodiment the actuator 160 is opaque, in variations to the illustrated embodiment the actuator 160 may be translucent or transparent. Nevertheless, it is preferable that the actuator 160 be substantially rigid.

The actuator 160 is operable to dispense the oral care fluid 112 through the first opening 130, as will be described below. A second opening 140 of the dispenser 2 is defined by and through a circumferential wall of the actuator 160, is in fluid communication with the exterior of the dispenser 2, and is at the proximal end portion of the dispenser 2. The second opening 140 also is in fluid communication with the second reservoir 120 via a check valve, or one-way valve, 150 that permits flow into the second reservoir 120 from the exterior of the dispenser 2 and restricts, preferably prevents, flow from the second reservoir 120 to the exterior of the dispenser 2. The check valve 150 is at a fixed location relative to the housing 100. In the illustrated embodiment, the check valve 150 comprises a diaphragm check valve 150. In other embodiments, the check valve 150 may comprise any one of a ball check valve, a swing check valve, and a duckbill check valve.

Although not present in the illustrated embodiment, in variations to the illustrated embodiment, the first opening 130 may be in fluid communication with the first reservoir 110 via a second check valve that restricts, preferably prevents, flow into the first reservoir 110 from the exterior of the dispenser 2 and permits flow from the first reservoir 110 to the exterior of the dispenser 2. Such a second check valve may comprise any one of diaphragm check valve, a ball check valve, a swing check valve, and a duckbill check valve.

The actuator 160 defines a chamber 162 of variable volume that fluidly connects the second opening 140 with the check valve 150. The actuator 160 is movably connected to the proximal end 100a of the housing 100 in such a way that the actuator 160 is movable relative to the housing 100 towards and away from the distal end 100b of the housing 100 in a direction parallel to a longitudinal axis of the housing 100. A resilient element, such as a coil spring, 180 is fixed between the proximal end 100a of the housing 100 and the actuator 160, so that the resilient element 180 connects the actuator 160 to the proximal end 100a of the housing 100, to bias the actuator 160 away from the distal end 100b of the housing 100. The connection between the actuator 160 and the housing 100 is such that the actuator 160 isolates the second reservoir 120 from the exterior of the dispenser 2, other than via the check valve 150, the chamber 162 and the second opening 140. The second reservoir 120 is in fluid communication with the exterior of the dispenser 2 only via the check valve 150, the chamber 162 and the second opening 140, in that order.

In FIGS. 5 and 6, the oral care dispenser 2 is shown with the actuator 160 in a first position relative to the housing 100. As mentioned above, the actuator 160 is operable to dispense the oral care fluid 112 through the first opening 130. More specifically, when the second opening 140 is blocked e.g. by a user's thumb or finger, the user can apply a force F, sufficient to overcome the resiliency of the resilient element 180, to the actuator 160 to move the actuator 160 towards the distal end 100b of the housing 100 and thus to reduce the volume of the chamber 162. This increases the pressure of air present in the chamber 162. As will be apparent to the skilled person on consideration of the full present disclosure, the increased pressure of the air in the chamber 162 causes the air in the chamber 162 to apply a force to the check valve 150 to overcome the resilience of the check valve 150. The air in the chamber 162 thus then passes through the check valve 150 into the second reservoir 120, which, in turn, increases the pressure of air present in the second reservoir 120. The increased pressure of the air in the second reservoir 120 causes the air in the second reservoir 120 to apply a force to the wall 104 of the piston to cause the piston to slide in the cavity 102 towards the distal end 100b of the housing 100, which causes the volume of the second reservoir 120 to increase and the volume of the first reservoir 110 to be reduced until the pressures in the first and second reservoirs 110, 120 are substantially equal. The reduction of the volume of the first reservoir 110 causes some of the oral care fluid 112 within the first reservoir 110 to be pushed through the first opening 130, and thus dispensed from the dispenser 2 to the exterior of the dispenser 2, such as onto a user's teeth or other surface in the oral cavity.

It will be understood that the actuator 160 thus is operable to dispense a predetermined metered volume or dose of the oral care fluid 112 through the first opening 130, so that the dispenser 2 is more easily operable to dispense a suitable volume of the oral care fluid 112. The predetermined metered volume is that volume of the oral care fluid 112 displaced from the first reservoir 110 by the increased volume of air introduced to the second reservoir 120, which in turn substantially equals the volume of air pushed from the chamber 162 of the actuator 160 into the second reservoir 120.

When the user subsequently unblocks the second opening 140 and reduces or removes the force F applied to the actuator 160, air is permitted to enter the chamber 162 via the second opening 140 and the resilience of the resilient element 180 causes the chamber 162 to expand, yet the check valve 150 prevents air returning from the second reservoir 120 into the chamber 162. The actuator 160 thus returns to the state shown in FIGS. 5 and 6.

In a variation to the oral care dispenser 2 illustrated in FIGS. 5 and 6, the piston of the oral care dispenser 2 may be replaced by with a wall 104 of flexible material that divides the cavity 102 into first and second reservoirs 110, 120, as per the oral care dispenser 1 of FIGS. 1 to 3. Such a variation to the oral care dispenser 2 would provide an embodiment of the oral care dispenser of the present invention. The wall 104 may comprise a bellows or a bag having a rim defining an orifice in fluid communication with the first opening 130, and a full circumference or perimeter of the rim may be fixed to the applicator 170 to isolate the first opening 130 and the first reservoir 110 from the second reservoir 120, or the full circumference or perimeter of the rim may be fixed to the inner surface of the housing 100 to isolate the first opening 130 and the first reservoir 110 from the second reservoir 120. In either case, the first reservoir 110 would be in fluid communication with the exterior of the dispenser only via the orifice and the first opening 130, in that order.

Figure 7A:
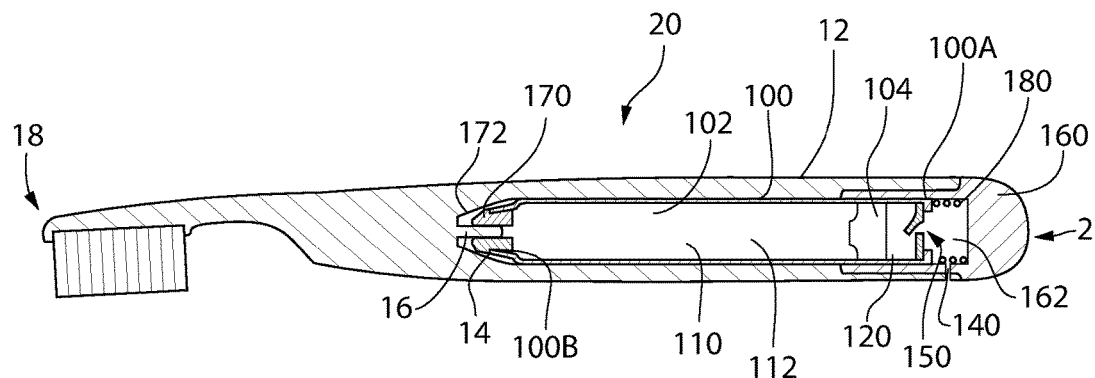
FIG. 7A shows a cross-sectional view of an oral care system according to another exemplary embodiment of the present invention, with an oral care dispenser of the system in a storage state relative to a toothbrush of the system.
Figure 7B:
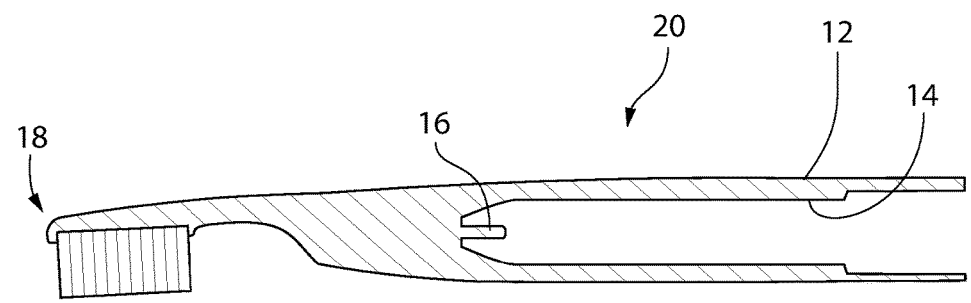
FIG. 7B shows a cross-sectional view of the oral care system of FIG. 7A, with the oral care dispenser in an application state relative to the toothbrush.
Figure 7B:
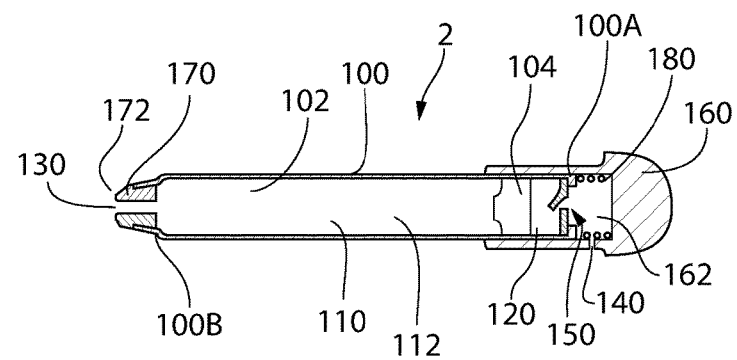

Cross sections of the oral care system of an exemplary embodiment of the present invention comprising the oral care dispenser 2 shown in FIGS. 5 and 6 are shown in FIGS. 7A and 7B. The oral care system comprises the oral care dispenser 2 and an oral care implement 20 comprising a toothbrush.

The toothbrush 20 comprises a handle 12, a cavity 14 in the handle 12 with an opening to an exterior of the toothbrush 10 at a first longitudinal end of the handle 12, and a head 18 comprising oral care elements, such as bristles, at a second longitudinal end of the handle 12. The oral care dispenser 2 is movable relative to the toothbrush 20 between a storage state, as shown in FIG. 7A, at which a portion of the toothbrush 20, namely a plug 16 within the cavity 14 in the handle 12 of the toothbrush 20, blocks the first opening 130 of the oral care dispenser 2 from an exterior of the oral care system, and an application state, as shown in FIG. 7B, at which the oral care dispenser 2 is detached from the toothbrush 20 and the first opening 130 of the oral care dispenser 2 is not blocked by the toothbrush 20. Moreover, when the oral care dispenser 2 is in the storage state, a portion of the toothbrush 20, namely part of the handle 12, blocks the second opening 140 of the oral care dispenser 2 from the exterior of the oral care system, and when the oral care dispenser 2 is in the application state, the second opening 140 of the oral care dispenser 2 is not blocked by the toothbrush 20. Thus, the oral care system has mechanisms that help prevent accidental actuation of the dispenser 2 to dispense some of the oral care fluid 112.

In variations to the embodiment shown in FIGS. 7A and 7B, the plug 16 may be omitted, and the first opening 130 may be blocked from the exterior of the oral care system by a portion of the cavity 14 forming a seal around the full perimeter or circumference of the applicator 170 or housing 100 of the dispenser 2. The toothbrush 20 and the dispenser 2 may comprise respective cooperating retaining members, for detachably locking or retaining the dispenser 2 in the storage state relative to the toothbrush 20.

The oral care dispenser 2 of the oral care system of FIGS. 7A and 7B may be varied as described above, by replacing the piston with a wall 104 of flexible material that divides the cavity 102 into first and second reservoirs 110, 120, as per the oral care dispenser 1 of FIGS. 1 to 3, so as to provide a variation to the illustrated embodiment of the oral care system shown in FIGS. 7A and 7B.

Figure 8:
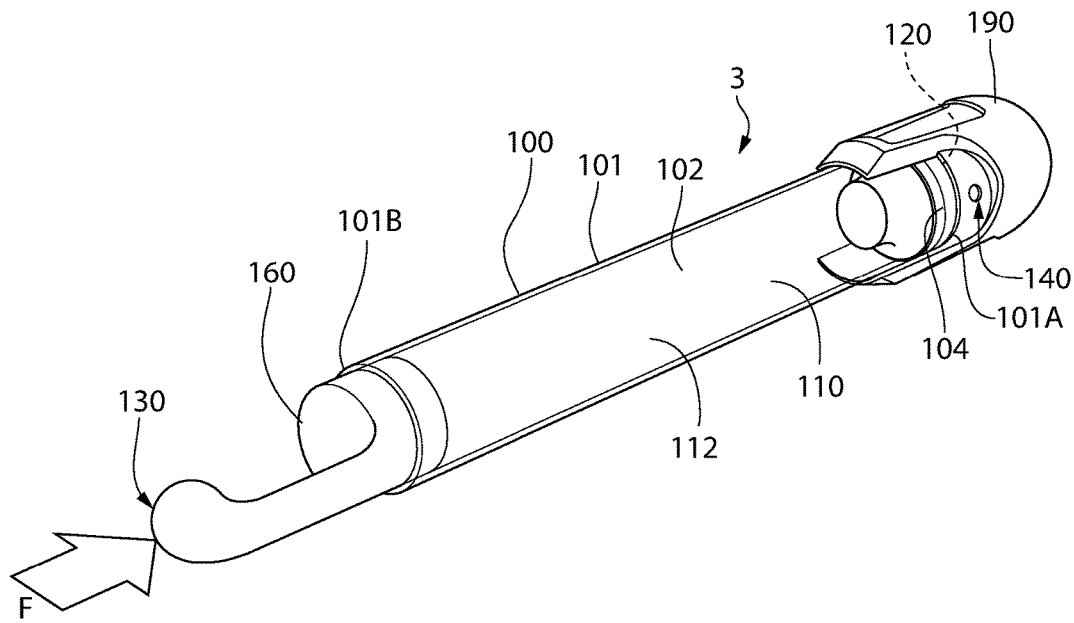
FIG. 8 shows a perspective view of an oral care dispenser according to a further exemplary embodiment of the present invention.
Figure 9:
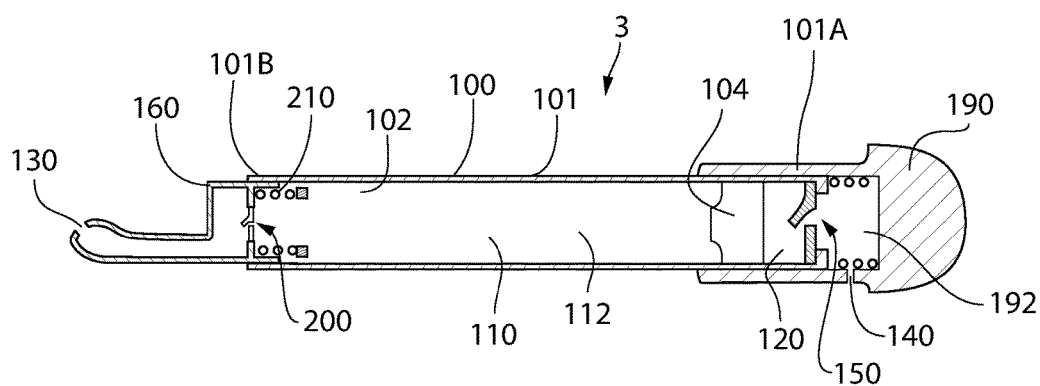
FIG. 9 shows a cross-sectional view of the oral care dispenser of FIG. 8.

FIGS. 8 and 9 illustrate an oral care dispenser according to a further exemplary embodiment of the present invention, generally designated with the reference numeral 3. Like reference numerals used in FIGS. 8 and 9 and FIGS. 5 and 6 indicate like components. The oral care dispenser 3 shares many features with the oral care dispenser 2.

The oral care dispenser 3 comprises a substantially rigid tube 101 formed of a plastic, specifically a thermoplastic polymer, more specifically polypropylene (PP). In some variations to the illustrated embodiment, the tube 101 may instead or additionally be formed of a different material, such as a different plastic or thermoplastic polymer. For example, the tube 101 may instead or additionally be formed of any one or more of the following materials: polypropylene (PP), polyethylene, polyamide, polyester, cellulosics, styrene-acrylonitrile (SAN), acrylic, and acrylonitrile butadiene styrene (ABS). While in the illustrated embodiment the tube 101 is transparent, in variations to the illustrated embodiment the tube 101 may be translucent or opaque. Nevertheless, it is preferable that the tube 101 be substantially rigid.

In the illustrated embodiment, the tube 101 extending between proximal and distal ends 101a, 101b of the tube 101 is defined by circular inner and outer surfaces. In other embodiments, the tube 101 may instead be defined by elliptical inner and outer surfaces, polygonal inner and outer surfaces, or irregular inner and outer surfaces.

The tube 101, and more specifically the inner surface of the tube 101, defines a cavity 102. In the illustrated embodiment, the cavity 102 has a circular cross-sectional shape. In other embodiments, the cross-sectional shape of the cavity 102 may instead be a different shape, such as elliptical, polygonal, or irregular. The cavity 102 is visible through the transparent material of the tube 101. Within the cavity 102 is a piston comprising a substantially rigid wall 104, which wall 104 divides the cavity 102 into first and second reservoirs 110, 120. Each of the first and second reservoirs 110, 120 is of variable volume, as will be better understood on consideration of the further description below.

The first reservoir 110 contains, indeed is full of, an oral care fluid 112 comprising one or more oral care agents. The oral care fluid 112 may be in any fluid form, such as a paste, a gel, or a liquid. In the illustrated embodiment, the oral care agent comprised in the oral care fluid is a whitening agent, such as peroxide containing tooth whitening compositions. However, any suitable oral care agent can be used in embodiments of the present invention. In variations to the illustrated embodiment, the oral care fluid may comprise one or more oral care agents selected from the group consisting of: antibacterial agents; oxidative or whitening agents; enamel strengthening or repair agents; tooth erosion preventing agents; tooth anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof. The oral care fluid preferably is free of (i.e., is not) toothpaste. Preferably, the oral care fluid is intended to provide supplemental oral care benefits in addition to merely brushing one's teeth.

At a distal end portion of the dispenser 3, and more specifically movably attached to the distal end 101b of the tube 101, the dispenser 3 comprises a rigid actuator 160 formed of a plastic, specifically a thermoplastic polymer, more specifically polypropylene (PP). In some variations to the illustrated embodiment, the actuator 160 may instead or additionally be formed of a different material, such as a different plastic or thermoplastic polymer. For example, the actuator 160 may instead or additionally be formed of any one or more of the following materials: polypropylene (PP), polyethylene, polyamide, polyester, cellulosics, styrene-acrylonitrile (SAN), acrylic, and acrylonitrile butadiene styrene (ABS). A first opening 130 of the dispenser 3 is defined by, indeed formed through, the actuator 160, and the first opening 130 is at the distal end portion of the dispenser 3. In the illustrated embodiment, a surface of the actuator 160 through which the first opening 130 passes is planar, but in other embodiments the surface could comprise a plurality of nubs or projections surrounding the first opening 130.

The first opening 130 is in fluid communication with the exterior of the dispenser 3 and with the first reservoir 110 via a first check valve, or one-way valve, 200 that restricts, preferably prevents, flow into the first reservoir 110 from the exterior of the dispenser 3 and permits flow from the first reservoir 110 to the exterior of the dispenser 3. The first check valve 200 is at a fixed location relative to and inside the actuator 160. In the illustrated embodiment, the first check valve 200 comprises a diaphragm check valve 200. In other embodiments, the first check valve 200 may comprise any one of a ball check valve, a swing check valve, and a duckbill check valve. The first reservoir 110 is in fluid communication with the exterior of the dispenser 3 only via the first check valve 200 and the first opening 130, in that order. The actuator 160 is operable to dispense the oral care fluid 112 through the first opening 130, as will be described below.

At a proximal end portion of the dispenser 3, and more specifically fixedly attached to the proximal end 101a of the tube 101, by adhesion or otherwise, the dispenser 3 comprises a rigid hood 190 formed of a plastic, specifically a thermoplastic polymer, more specifically polypropylene (PP). In some variations to the illustrated embodiment, the hood 190 may instead or additionally be formed of a different material, such as a different plastic or thermoplastic polymer. For example, the hood 190 may instead or additionally be formed of any one or more of the following materials: polypropylene (PP), polyethylene, polyamide, polyester, cellulosics, styrene-acrylonitrile (SAN), acrylic, and acrylonitrile butadiene styrene (ABS). While in the illustrated embodiment the hood 190 is opaque, in variations to the illustrated embodiment the hood 190 may be translucent or transparent. Nevertheless, it is preferable that the hood 190 be substantially rigid. Together, the hood 190 and the tube 101 form, or are comprised in, a housing 100 of the dispenser 3. In some embodiments, the hood 190 is integral with the tube 101.

A second opening 140 of the dispenser 3 is defined by and through a circumferential wall of the hood 190 of the housing 100, is in fluid communication with the exterior of the dispenser 3, and is at the proximal end portion of the dispenser 3. The second opening 140 also is in fluid communication with the second reservoir 120 via a second check valve, or one-way valve, 150 that permits flow into the second reservoir 120 from the exterior of the dispenser 3 and restricts, preferably prevents, flow from the second reservoir 120 to the exterior of the dispenser 3. The second check valve 150 is at a fixed location relative to the tube 101 and relative to the hood 190. In the illustrated embodiment, the second check valve 150 comprises a diaphragm check valve 150. In other embodiments, the second check valve 150 may comprise any one of a ball check valve, a swing check valve, and a duckbill check valve.

The hood 190 defines a chamber 192 of fixed volume that fluidly connects the second opening 140 with the second check valve 150. The connection between the hood 190 and the tube 101 is such that the hood 190 isolates the second reservoir 120 from the exterior of the dispenser 3, other than via the second check valve 150, the chamber 192 and the second opening 140. The second reservoir 120 is in fluid communication with the exterior of the dispenser 3 only via the second check valve 150, the chamber 192 and the second opening 140, in that order.

The actuator 160 is movably connected to the distal end 101b of the tube 101 in such a way that the actuator 160 is movable relative to the tube 101 towards and away from the proximal end 101a of the tube 101 in a direction parallel to a longitudinal axis of the tube 101. A resilient element, such as a coil spring, 210 is fixed between the distal end 101b of the tube 101 and the actuator 160, so that the resilient element 210 connects the actuator 160 to the distal end 101b of the tube 101, to bias the actuator 160 away from the proximal end 101a of the tube 101.

In FIGS. 8 and 9, the oral care dispenser 3 is shown with the actuator 160 in a first position relative to the tube 101. As mentioned above, the actuator 160 is operable to dispense the oral care fluid 112 through the first opening 130. More specifically, when a user applies a force F, sufficient to overcome the resiliency of the resilient element 200, to the actuator 160 to move the actuator 160 towards the proximal end 101a of the tube 101, the check-valve 150 prevents a flow of air from the second reservoir 120 through the second opening 140 via the chamber 192. Although the applied force F may cause air in the second reservoir 120 to be slightly compressed, the piston 140 and air in the second reservoir 120 apply, to the oral care fluid 112 in the first reservoir 110, a force opposing the applied force F. Accordingly, the volume of the first reservoir 110 is reduced, which causes some of the oral care fluid 112 within the first reservoir 110 to be pushed through the second check valve 200 and the first opening 130, and thus dispensed from the dispenser 3 to the exterior of the dispenser 3, such as onto a user's teeth or other surface in the oral cavity.

With the second opening 140 unblocked, when the user reduces or removes the force F applied to the actuator 160, the biasing force of the resilient element 210 causes the actuator 160 to move in a direction away from the proximal end 101a of the tube 101. This reduces the pressure in the first reservoir 110 to below that in the chamber 162, which causes air in the chamber 162 to apply a force to the second check valve 150 to overcome the resilience of the second check valve 150. Thus, air in the chamber 162 is pulled into the second reservoir 120 through the second check valve 150. In turn, this causes air to be pulled into the chamber 162 via the second opening 140 until the pressures in the first reservoir 110 and the chamber 162 are substantially equal. The actuator 160 thus returns to the state shown in FIGS. 8 and 9.

It will be understood that the actuator 160 thus is operable to dispense a predetermined metered volume or dose of the oral care fluid 112 through the first opening 130, so that the dispenser 3 is more easily operable to dispense a suitable volume of the oral care fluid 112. The predetermined metered volume is that volume of the oral care fluid 112 displaced from the first reservoir 110 by the reduction in volume of the first reservoir 110 by movement of the actuator 160 relative to the housing 100.

In a variation to the oral care dispenser 3 illustrated in FIGS. 8 and 9, the second opening 140 may be defined elsewhere than by and through the circumferential wall of the hood 190. For example, the second opening 140 may be provided at the proximal-most end of the dispenser 3, i.e. through the apex of the hood 190.

In another variation to the oral care dispenser 3 illustrated in FIGS. 8 and 9, the piston of the oral care dispenser 3 may be replaced by with a wall 104 of flexible material that divides the cavity 102 into first and second reservoirs 110, 120, as per the oral care dispenser 1 of FIGS. 1 to 3. Such a variation to the oral care dispenser 3 would provide an embodiment of the oral care dispenser of the present invention. The wall 104 may comprise a bellows or a bag having a rim defining an orifice in fluid communication with the first opening 130, and a full circumference or perimeter of the rim may be fixed to the actuator 160 to isolate the first opening 130 and the first reservoir 110 from the second reservoir 120, or the full circumference or perimeter of the rim may be fixed to the inner surface of the tube 101 to isolate the first opening 130 and the first reservoir 110 from the second reservoir 120. In either case, the first reservoir 110 would be in fluid communication with the exterior of the dispenser only via the orifice, the first check valve 200, and the first opening 130, in that order.

An oral care system according to a further exemplary embodiment of the present invention comprises the oral care dispenser 3 shown in FIGS. 8 and 9 and an oral care implement, such as a toothbrush. The oral care system may be the same as that shown in FIGS. 7A and 7B, except for a change of shape of the cavity of the toothbrush to accommodate the actuator 160 of the oral care dispenser 3 in place of the applicator 170 of the oral care dispenser 2. Moreover, the oral care system may be operable in the same way as the system shown in FIGS. 7A and 7B, so that the oral care dispenser 3 is movable relative to the toothbrush between a storage state, at which respective portions of the toothbrush block the first and second openings 130, 140 of the oral care dispenser 3 from an exterior of the oral care system, and an application state, at which the oral care dispenser 3 is detached from the toothbrush and the first and second openings 130, 140 of the oral care dispenser 3 are not blocked by the toothbrush. Thus, the oral care system may have mechanisms that help prevent accidental actuation of the dispenser 3 to dispense some of the oral care fluid 112.

The above-described possible variations to the oral care system shown in FIGS. 7A and 7B are equally applicable to the oral care system comprising the oral care dispenser 3 shown in FIGS. 8 and 9 and the oral care implement.

In respective variations to each of the oral care systems described herein, the oral care dispenser of the system may remain attached, such as via a hinge, to the oral care implement of the system when the oral care dispenser is in the application state.

What is claimed is:

1. An oral care dispenser comprising:
a housing defining a cavity;
a wall of flexible material in the cavity, the wall dividing the cavity into first and second reservoirs of variable volume, the first reservoir containing an oral care fluid;
a first opening in fluid communication with the first reservoir, wherein the oral care fluid is dispensable from the dispenser through the first opening;
a second opening in fluid communication with the second reservoir via a check valve located between the second opening and the second reservoir, the check valve permitting flow of air into the second reservoir from an exterior of the dispenser and restricting flow of air from the second reservoir to the exterior of the dispenser; and
an actuator operable to dispense the oral care fluid through the first opening.

2. The oral care dispenser of claim 1, wherein the actuator is operable to push air into the second reservoir through the check valve.

3. The oral care dispenser of claim 2, wherein the actuator comprises a wall defining the second opening and a chamber fluidly connecting the second opening with the check valve.

4. The oral care dispenser of claim 3, wherein the chamber is of variable volume, and the actuator is operable to reduce the volume of the chamber when the second opening is blocked, thereby to push air from the chamber into the second reservoir through the check valve.

5. The oral care dispenser of claim 4, wherein the actuator comprises flexible material defining the chamber of variable volume.

6. The oral care dispenser of claim 1, wherein the actuator comprises the second opening and is movable relative to the housing to reduce the volume of the first reservoir, thereby to dispense the oral care fluid through the first opening.

7. The oral care dispenser of claim 1, wherein the wall of flexible material comprises a deformable vessel with an orifice in fluid communication with the first opening, and wherein the vessel is deformable according to a predetermined pattern of collapse.

8. The oral care dispenser of claim 1, wherein the first opening is in fluid communication with the first reservoir via a second check valve that restricts flow into the first reservoir from an exterior of the dispenser and permits flow from the first reservoir to the exterior of the dispenser.

9. The oral care dispenser of claim 1, comprising a flexible or resilient applicator, wherein the first opening is formed in the applicator.

10. The oral care dispenser of claim 1, wherein the first opening is at a distal end portion of the dispenser and the second opening is at a proximal end portion of the dispenser.

11. An oral care dispenser comprising:
a housing defining a cavity;
a wall in the cavity, the wall dividing the cavity into first and second reservoirs of variable volume, the first reservoir containing an oral care fluid;

a first opening in fluid communication with the first reservoir, wherein the oral care fluid is dispensable from the dispenser through the first opening;

a second opening in fluid communication with the second reservoir via a check valve that permits flow into the second reservoir from an exterior of the dispenser and restricts flow from the second reservoir to the exterior of the dispenser; and an actuator operable to dispense the oral care fluid through the first opening;

wherein the actuator comprises the second opening and is movable relative to the housing to reduce the volume of the first reservoir, thereby to dispense the oral care fluid through the first opening.

12. The oral care dispenser of claim 11, wherein the wall comprises a wall of flexible material.

13. The oral care dispenser of claim 11, wherein the actuator is operable to pull air into the second reservoir through the check valve.

14. The oral care dispenser of claim 11, wherein the actuator comprises the second opening, the check valve, and a chamber located between the second opening and the check valve, and wherein the check valve is located between the chamber and the second reservoir.

15. An oral care system, comprising:
  an oral care dispenser comprising:
    a housing defining a cavity;
    a wall in the cavity, the wall dividing the cavity into first and second reservoirs of variable volume, the first reservoir containing an oral care fluid;
    a first opening in fluid communication with the first reservoir, wherein the oral care fluid is dispensable from the dispenser through the first opening;
    a second opening in fluid communication with the second reservoir; and
    an actuator operable to dispense the oral care fluid through the first opening; and
  an oral care implement;
  wherein the oral care dispenser is movable relative to the oral care implement between a storage state, at which a portion of the oral care implement blocks the second opening of the oral care dispenser from an exterior of the oral care system, and an application state, at which the second opening of the oral care dispenser is not blocked by the oral care implement.

16. The oral care system of claim 15, wherein the wall comprises a wall of flexible material.

17. The oral care system of claim 15, wherein the second opening is in fluid communication with the second reservoir via a check valve that permits flow into the second reservoir from an exterior of the dispenser and restricts flow from the second reservoir to the exterior of the dispenser.

18. The oral care system of claim 15, wherein, when the oral care dispenser is in the storage state, a portion of the oral care implement blocks the first opening of the oral care dispenser from the exterior of the oral care system, and, when the oral care dispenser is in the application state, the first opening of the oral care dispenser is not blocked by the oral care implement.

19. The oral care system of claim 15, wherein, when the oral care dispenser is in the application state, the oral care dispenser is detached from the oral care implement.

20. The oral care system of claim 15, wherein the oral care implement comprises a toothbrush.

* * * * *